US012759991B2

(12) United States Patent
Hu et al.

(10) Patent No.: US 12,759,991 B2
(45) Date of Patent: Oct. 13, 2026

(54) SMALL MOLECULE COMPOUND AND USE AND COMPOSITION THEREOF

(71) Applicant: SOOCHOW UNIVERSITY, Suzhou (CN)

(72) Inventors: Yanwei Hu, Suzhou (CN); Yi Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 383 days.

(21) Appl. No.: 18/035,491

(22) PCT Filed: Aug. 4, 2021

(86) PCT No.: PCT/CN2021/110612

§ 371 (c)(1),
(2) Date: Jun. 28, 2023

(87) PCT Pub. No.: WO2022/188347

PCT Pub. Date: Sep. 15, 2022

(65) Prior Publication Data

US 2023/0391742 A1 Dec. 7, 2023

(30) Foreign Application Priority Data

Mar. 8, 2021 (CN) ........................ 202110249831.2

(51) Int. Cl.

| | |
|---|---|
| ***C07D 317/54*** | (2006.01) |
| ***A61K 31/704*** | (2006.01) |
| ***A61K 33/243*** | (2019.01) |
| ***A61P 35/00*** | (2006.01) |

(52) U.S. Cl.
CPC .......... *C07D 317/54* (2013.01); *A61K 31/704* (2013.01); *A61K 33/243* (2019.01); *A61P 35/00* (2018.01)

(58) Field of Classification Search
CPC ............................... C07D 317/54; A61P 35/00
See application file for complete search history.

(56) References Cited

FOREIGN PATENT DOCUMENTS

| | | | | |
|---|---|---|---|---|
| CN | 105726527 A | | 7/2016 | |
| CN | 110152001 A | | 8/2019 | |
| CN | 112851627 A | | 5/2021 | |
| EP | 1127883 A2 | * | 8/2001 | .............. A61P 43/00 |

* cited by examiner

*Primary Examiner* — Andrew D Kosar
*Assistant Examiner* — John D Mcanany
(74) *Attorney, Agent, or Firm* — SZDC Law PC

(57) ABSTRACT

Disclosed in the present invention are a small molecule compound and use and a composition thereof. The use of the small molecule compound is specifically as follows: 4-((2-(4-(tert-butyl)phenoxy)acetyl)glycyl)phenyl benzo[d][1,3] dioxane-5-carboxylate, or a pharmaceutically, healthcare or food acceptable salt or ester or derivative thereof, or a mixture thereof for preparing substances for treating tumors, inhibiting tumor cell growth and/or inducing tumor cell apoptosis. The composition contains: (1) a compound 4-((2-(4-(tert-butyl)phenoxy)acetyl)glycyl)phenyl benzo[d][1,3] dioxane-5-carboxylate, or a pharmaceutically, healthcare or food acceptable salt or ester or derivative thereof, or a mixture thereof; (2) an apoptosis-causing drug; and (3) a pharmaceutically, healthcare or food acceptable carrier or excipient.

10 Claims, 4 Drawing Sheets

SMALL MOLECULE COMPOUND AND USE AND COMPOSITION THEREOF

This application is the National Stage Application of PCT/CN2021/110612, filed on Aug. 4, 2021, which claims priority to Chinese Patent Application No. 202110249831.2, filed on Mar. 8, 2021, which is incorporated by reference for all purposes as if fully set forth herein.

TECHNICAL FIELD

The invention relates to the fields of biotechnology and medicine, and in particular, a small molecular compound that specifically inhibits NAC1 protein through design and synthesis based on bioinformatics and computer technology. The present invention also relates to a pharmaceutical composition containing the small molecule compound, and discloses a method for using the compound for the treatment of diseases, especially the use in the treatment of malignant tumors.

BACKGROUND TECHNIQUE

Malignant tumors are a class of diseases that endanger human health. With the development of tumor molecular biology, genomics, and proteomics, a large number of regulatory factors that play a key role in tumorigenesis and development have been revealed. On this basis, a major change in the concept of anti-tumor drug research and development has emerged. The focus of research and development is shifting from traditional cytotoxic drugs to targeting key regulators in the process of tumor development. These new drugs target the differences between normal cells and tumor cells, and can achieve highly selective and low toxicity therapeutic effects, thereby overcoming traditional cytotoxic drugs' disadvantages, such as poor selectivity, serious toxic and side effects, and easy development of drug resistance. For this reason, tumor targeted therapy has entered a new stage of research and development. In recent years, with the development of molecular biology and X-ray crystallography, the three-dimensional structures of a large number of tumor-related biological macromolecules have been determined; the rapid development of computational science has led to the emergence of computer-aided drug design, which has been applied into the development of new drugs. The new development greatly improves the success rate of drug research and development, reduces research and development costs, and shortens the research and development cycle. It has now become one of the core technologies of innovative drug research.

The BTB/POZ family gene NACC1 gene encodes the expression of cellular transcription factor NAC1 (nucleus accumbens-1), which is located in the human chromosome region Ch19p13.2, and is a newly discovered oncogenic factor. NAC1 is generally highly expressed in various gynecological tumors (such as ovarian cancer, cervical cancer, endometrial cancer, breast cancer, etc.), but not in normal tissues. The BTB domain (also known as the POZ domain) is an important domain that mediates protein interactions, and the BZB domain (1-129 amino acid sequence) of NAC1 is required for the formation of the NAC1 dimer complex, which forms the NAC1 dimer aggregate complexes can participate in the regulation of various biological functions, such as anti-apoptosis, pro-proliferation, pro-invasion and metastasis, and anti-aging.

Experiments have shown that NAC1 is involved in inhibiting the apoptosis of ovarian cancer cells induced by cisplatin and paclitaxel, and the escape of apoptotic signals is closely related to the occurrence and development of tumors. Since NAC1 is only highly expressed in tumor cells and is involved in tumor resistance to apoptotic signals, small-molecule compounds targeting this molecule may be able to abolish its apoptosis-inhibiting function, and may be combined with cisplatin, paclitaxel, etc. Combination of chemotherapeutic drugs opens up a new strategy for tumor treatment.

At present, although some compounds that inhibit tumor growth have been developed, there is still a need to develop new compounds that inhibit tumor growth or induce tumor cell apoptosis.

SUMMARY OF THE INVENTION

The object of the present invention is to provide a compound that inhibits tumor cell growth or induces tumor cell apoptosis, and another object of the present invention is to provide a pharmaceutical composition prepared from the compound.

An embodiment of the present invention includes:

4-((2-(4-tert-butyl)phenoxy)acetyl)glycyl)phenylbenzo[d][1,3]dioxane-5-carboxylate, having the following structure:

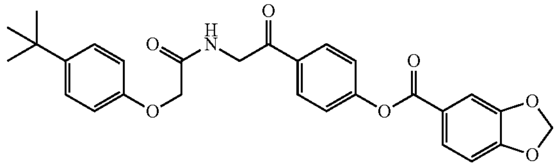 [SMILES: CC(C)(C)c1ccc(OCC(=O)NCC(=O)c2ccc(OC(=O)c3ccc4c(c3)OCO4)cc2)cc1]
,

A synthetic route thereof is:

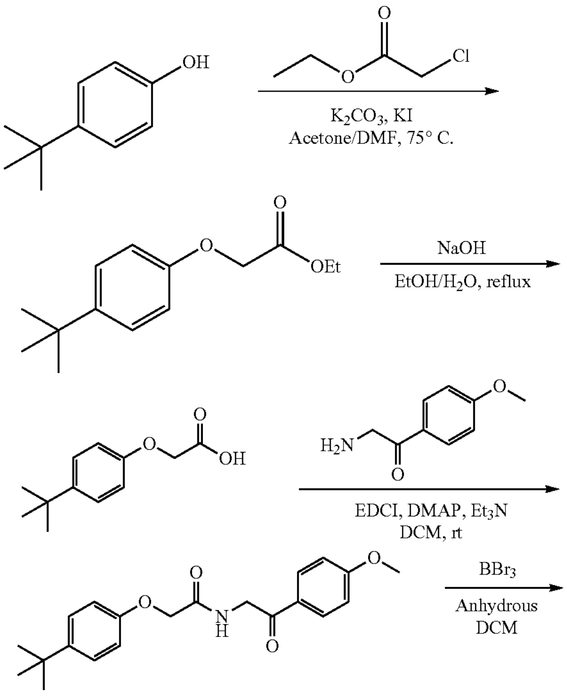

-continued

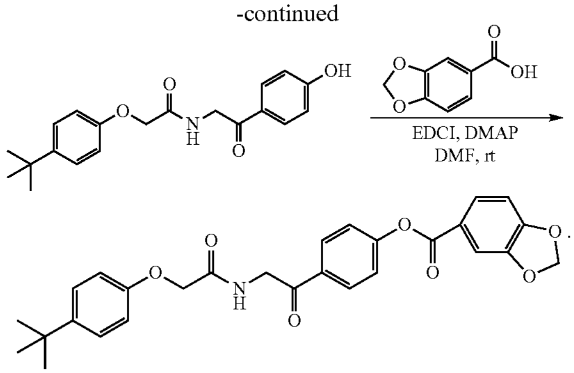

NAI-008

Another embodiment of the present invention includes:

Use of 4-((2-(4-(tert-butyl)phenoxy)acetyl)glycyl)phenylbenzo[d][1,3]-dioxane-5-carboxylate, a pharmaceutical, nutraceutical or food science acceptable salt, ester or derivative thereof, or a mixture thereof, in preparing of medicaments for treating tumors, inhibiting tumor cell growth, and/or inducing tumor cell apoptosis.

Preferably, the use is for preparing an inhibitor of human nucleus accumbens 1.

Preferably, the tumor cell is a tumor cell expressing human nucleus accumbens 1, and an expression level of the human nucleus accumbens 1 of the tumor cells is 30%-50% higher than that of a normal cell.

Preferably, the tumor cell is selected from the group consisting of a breast cancer cell, a lung cancer cell, a stomach cancer cell, a prostate cancer cell, an ovarian cancer cell, a colon cancer cell, a liver cancer cell, a cervical cancer cell, an endometrial cancer cell, or a B lymphoid tumor cell. More preferably, the tumor cell is selected from the group consisting of an ovarian cancer cell, a cervical cancer cell, a breast cancer cell, and an endometrial cancer cell. Even more preferably, the tumor cell is an ovarian cancer cell.

Another embodiment of the present invention includes:

The present application discloses a composition, and the composition includes:

(1) 4-((2-(4-(tert-butyl)phenoxy)acetyl)glycyl)phenylbenzo[d][1,3]-dioxane-5-carboxylate, a pharmaceutical, nutraceutical or food science acceptable salt, ester or derivative thereof, or a mixture thereof;

(2) an apoptotic drug; and (3) a pharmaceutical, nutraceutical, or food science acceptable carrier or excipient. Preferably, the apoptosis-inducing drug is carboplatin, doxorubicin, tamoxifen, 5-fluorouracil, bisfuran fluorouracil, harringtonine, cytarabine, flutamide, ifosfamide, deoxyfluridine, loboplatin, letrozole, teniposide, angiostatin, endostatin or avastin, etc. More preferably, the apoptosis-inducing drug is cisplatin or doxorubicin.

Preferably, a weight ratio of 4-((2-(4-(tert-butyl)phenoxy)acetyl)glycyl)phenyl-benzo[d][1,3]-dioxane-5-carboxylate and the apoptotic drug is 1:500-500:1; more preferably, 1:100-100:1; and even more preferably, 1:50-50:1.

Preferably, 4-((2-(4-(tert-butyl)phenoxy)acetyl)glycyl)phenylbenzo[d][1,3]-dioxane-5-carboxylate is 1-95 wt % of a total weight of the composition; more preferably, 5-90 wt %; and even more preferably, 10-80 wt %.

Preferably, a dosage form of the composition is tablet, capsule, powder, granule, suspension, or injection. When the composition is in unit dosage form or multi-dosage form, the content of the compound, its pharmaceutically or nutraceutical acceptable salt or ester, or their mixture is 0.05-50000 mg/dose; preferably 0.1-10000 mg/dose, more preferably 0.5-5000 mg/dose.

The advantages of the present invention are:

(a) The small molecule compound designed for the human NAC1 protein of the present invention can effectively target and inhibit the anti-apoptotic molecule-NAC1 protein, and thus be used for cancer treatment;

(b) The small molecule compound of the present invention can also be combined with other drugs and treatment methods for the treatment of malignant tumors;

(c) The small molecule compound of the present invention has the advantages of good permeability, lower toxic and side effects, simple structure and synthetic route.

DETAILED DESCRIPTION

Figure 1:
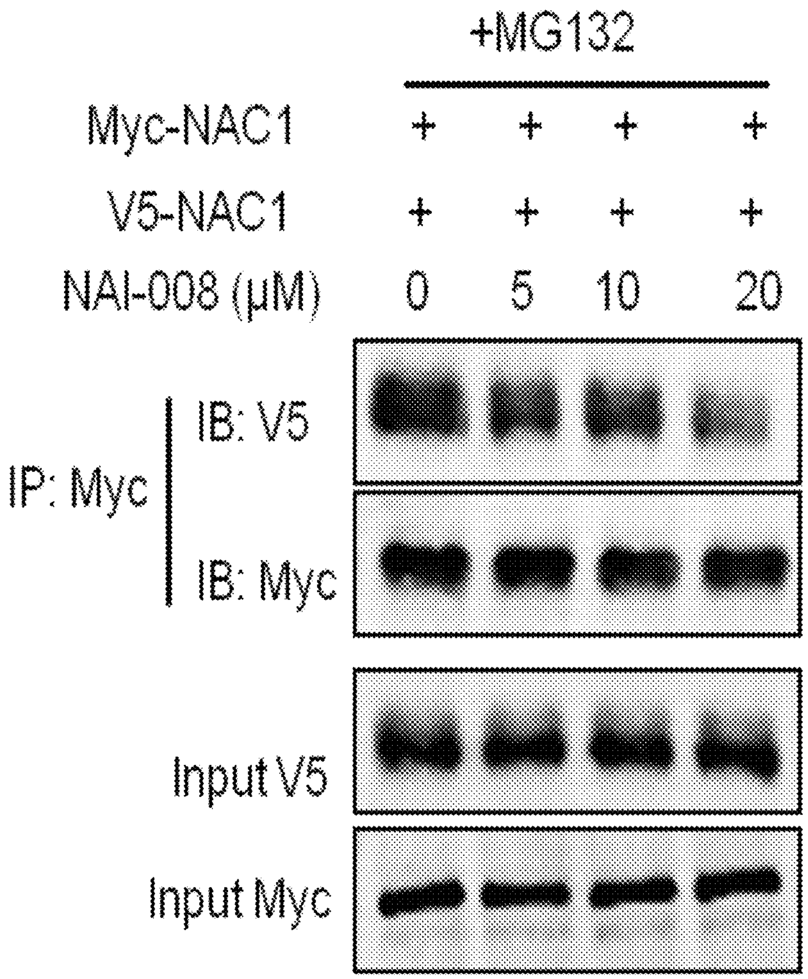
FIG. 1 shows that compound NAI-008 inhibits the formation of NAC1 protein dimer.

After extensive and in-depth research, it was found that the expression of NAC1 in some tumor cells is often increased, and inhibiting the expression and function of NAC1 can inhibit the proliferation of tumor cells and the tumorigenic activity in vitro and in vivo. To this end, the inventors designed and synthesized several small-molecule compounds that may bind to NAC1 with the help of computer-aided drugs, and then used in vitro binding experiments and MTT methods to screen these compounds for the second round. Compound NAI-008, a small molecule compound 4-((2-(4-(tert-butyl)phenoxy)acetyl)glycyl)phenylbenzo[d][1,3]dioxane-5-carboxylate, which strongly enhances the inhibitory effect of cisplatin on the proliferation of ovarian cancer cell line SKOV3.

Specifically, the inventors' research shows that NAC1 is selectively highly expressed in ovarian cancer tumor tissue, but not expressed in normal ovarian epithelial tissue, suggesting that NAC1 may be closely related to tumorigenesis and growth. In ES2 ovarian cancer cell lines with low NAC1 expression, overexpression of NAC1 can significantly resist cisplatin-induced apoptosis and promote cell growth, suggesting that it may be an anti-apoptotic molecule. In ovarian cancer tumor cells with high expression of NAC1, inhibiting the expression of NAC1 can enhance the sensitivity of ovarian cancer cells to cisplatin-induced apoptosis and inhibit the ability of tumor cells to form clones. It is suggested that NAC1 is likely to be a target for the treatment of ovarian cancer. The inventors' research shows that the anti-apoptotic NAC1 molecule plays an important role in the process of cell growth regulation, cell apoptosis, tumor occurrence and development, and the like. Therefore, NAC1 is likely to serve as a potential candidate target in the diagnosis and treatment of clinical tumors.

On this basis, the inventors designed and synthesized a large number of compounds, thereby obtaining a small molecule compound that can effectively inhibit tumors. The small molecule compound specifically targets the anti-apoptotic molecule-NAC1 protein at the protein level, and intervenes in the biological behavior of tumor cells expressing NAC1, thereby effectively inhibiting the function of NAC1 and achieving anti-tumor effect.

The details are as follows:

As used herein, the terms "small molecule compound of the present invention," "compound NAI-008" or "compound of the present invention," "m-amidobenzamide derivative of the present invention" are used interchangeably and all refer to small molecule compound 4-((2-(4-(tert-butyl)phenoxy)acetyl)glycyl)phenylbenzo[d][1,3]-dioxane-5-carboxylate, a pharmaceutical acceptable salt, or active derivative thereof.

4-((2-(4-(tert-butyl)phenoxy)acetyl)glycyl)phenylbenzo[d][1,3]dioxane-5-carboxylate is a compound that targets human nucleus accumbens 1 protein (NAC1) and has the following structural formula:

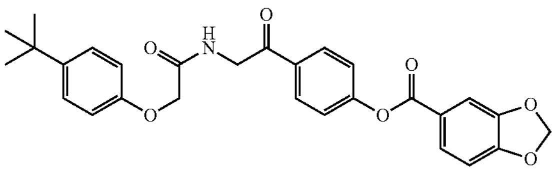

The above compound is a new compound, which can be prepared by conventional organic synthesis methods.

1. Active Ingredient

In the present invention, a preferred "active ingredient" refers to a small molecule compound that can bind to human NAC1 protein, and that a combination with cisplatin can reduce the growth of ovarian cancer SKOV3 cells to 50% % or less (i.e., at least a 50% reduction), preferably to 38% or less, more preferably to 35% or less, or to a range between the above values as endpoints.

The m-amidobenzamide derivative used in the present invention may be used in the form of salts derived from pharmaceutically or physiologically acceptable acids or bases. These salts include, but are not limited to, salts with inorganic acids, such as hydrochloric, sulfuric, nitric, or phosphoric; salts with organic acids, such as acetic, oxalic, succinic, or maleic; and others salts, including but not limited to, salts formed with alkali or alkaline earth metals, such as sodium, potassium, calcium or magnesium. A particularly preferred class of salts are the sodium or potassium salts.

The present invention also includes the compounds of the present invention in the form of esters (e.g., carbamates) or other conventional "prodrugs" that, when administered in this form, are converted to the active moiety in vivo.

The small molecule compound of the present invention can effectively inhibit the function of human NAC1 protein, thereby inhibiting the proliferation of tumor cells and promoting the apoptosis of tumor cells. Specifically, the small molecule compound of the present invention targets human NAC1 protein at the molecular level, and reverses the biological behavior of tumor cells that positively express human NAC1 protein. Experiments have shown that: (1) inhibiting the expression and function of NAC1 can inhibit the proliferation of tumor cells and promote tumor cell apoptosis; (2) inhibiting the expression and function of NAC1 in vivo can inhibit the tumorigenicity of tumor cells in vitro; (3) inhibiting the expression and function of NAC1 can inhibit the growth of tumor cells in vivo.

2. Pharmaceutical Composition

The present invention also includes pharmaceutical compositions containing meta-amidobenzamide derivatives and pharmaceutically acceptable salts or esters thereof. The m-amidobenzamide derivatives and the pharmaceutical compositions thereof of the present invention can be used for treating cancer tumors, that is, administering a safe and effective amount of the m-amidobenzamide derivatives to mammals.

The compounds of the present invention can be used in combination with other chemotherapeutic agents, such as paclitaxel, carboplatin, doxorubicin, tamoxifen, 5-fluorouracil, difurofluorouracil, harringtonine, cytarabine, flutamide, ifosfamide, deoxyfluridine, loboplatin, letrozole or teniposide, etc.; tumor angiostatic drugs, such as angiostatin, endostatin, avastin, etc., and can control, alleviate or cure diseases by inhibiting NAC1, such as ovarian cancer and other cancers. In addition, the compounds of the present invention can also be used in combination with anti-tumor traditional Chinese medicines (or their preparations).

A preferred pharmaceutical composition also includes an apoptotic drug, such as cisplatin and the like.

When the m-amidobenzamide derivative or a pharmaceutically acceptable salt or ester thereof is used to treat tumors, it can be mixed with one or more pharmaceutically acceptable carriers or excipients, such as solvents, diluents etc., to form a pharmaceutical composition.

Liquid carriers include sterile water, polyethylene glycols, nonionic surfactants, and edible oils (e.g., corn oil, peanut oil, and sesame oil). Solid carriers include starch, lactose, dibasic calcium phosphate, microcrystalline cellulose, sucrose and kaolin, as appropriate to the identity of the active ingredient and the particular mode of administration desired. Adjuvants commonly used in the preparation of pharmaceutical compositions may also advantageously be included, such as flavors, colors, preservatives and antioxidants, such as vitamin E, vitamin C, 2,6-di-tert-butyl-p-cresol (BHT) and tert-butylhydroxyanisole (BHA).

Generally, the pharmaceutical compositions of the present invention include the following dosage forms: oral administration dosage forms, such as tablets, capsules, dispersible powders, granules or suspensions (suspensions) (containing, for example, about 0.05-5% suspending agents (cosolvents)), syrups (containing, for example, about 10-50% sugar), and elixirs (containing about 20-50% ethanol); or as sterile injectable solutions or suspensions (containing about 0.05-5% in an isotonic medium cosolvent) for parenteral administration. These pharmaceutical preparations may generally contain about 0.001-99.9 wt %, preferably 0.5-99.5 wt %, preferably 2.5-90 wt %, more preferably 5-60 wt % of the active ingredient (m-amidobenzamide derivatives or pharmaceutically acceptable salts or esters thereof) mixed with a carrier, based on the total weight of the composition.

In preparing pharmaceutical compositions, generally, the compounds of the present invention can be formulated in a non-toxic, inert and pharmaceutically acceptable aqueous carrier medium, usually at a pH of about 5-8, preferably at a pH of about 6-8, although pH can vary depending on the nature of the substance being formulated and the condition being treated.

The formulated pharmaceutical compositions can be administered by conventional routes, including, but not limited to, intratumoral, intramuscular, intraperitoneal, intravenous, subcutaneous, intradermal, oral or topical administration. Intravenous administration is preferred.

The m-amidobenzamide derivatives used in the present invention can also be administered parenterally or intraperitoneally. Solutions or suspensions of these active compounds (as the free base or as a pharmaceutically acceptable salt) can also be prepared in water suitably mixed with a surfactant, such as hydroxypropylcellulose. Dispersions can also be prepared in glycerol, liquids, polyethylene glycols, and mixtures thereof in oils. Under ordinary conditions of storage and use, these preparations contain a preservative to prevent the growth of microorganisms.

The pharmaceutical forms suitable for injection include sterile aqueous solutions or dispersions and sterile powders for the extemporaneous preparation of sterile injectable solutions or dispersions. In all cases, these forms must be sterile and must be fluid for easy syringe expelling. Thye must be stable under the conditions of manufacture and storage and must be resistant to the contaminating influence of microorganisms such as bacteria and fungi. The carrier can be a solvent or dispersion medium containing, for example, water, alcohol (for example, glycerol, propylene glycol, and liquid polyethylene glycol), suitable mixtures thereof, and vegetable oils.

When using the N-acetylated phenoxyacetamide derivatives of the present invention, it can also be used in combination with other tumor treatment methods (such as radiotherapy) or other therapeutic agents (such as cisplatin, doxorubicin, etc.).

The effective dose of active ingredient employed may vary with the mode of administration and the severity of the disease to be treated. Typically, however, when a compound of the present invention is administered at a daily dose of about 0.01-100 mg/kg animal body weight (preferably 0.02-20 mg/kg body weight, more preferably 0.1-10 mg/kg body weight). For satisfactory results, it is preferably administered in a dose of 1-4 times a day, or in a sustained release form. For most large mammals, the total daily dose is about 5-5000 mg or more, preferably 10-1000 mg. Dosage forms suitable for oral administration include about 0.5-500 mg of the active compound in admixture with a solid or liquid pharmaceutically acceptable carrier. This dosage regimen can be adjusted to provide the best therapeutic response. For example, several divided doses may be administered daily, or the dose may be proportionally reduced, as dictated by the exigencies of the therapeutic situation.

From the standpoint of ease of preparation and administration, the preferred pharmaceutical compositions are liquid compositions. Intravenous administration of the meta-amidobenzamide derivatives is preferred.

3. Nutraceutical Composition

In addition to preparing pharmaceutical compositions for treating tumors, in the present invention, m-amidobenzamide derivatives or pharmaceutically acceptable salts or esters or extracts thereof can also be used for preparing nutraceutical compositions for adjuvant therapy of tumors.

In the present invention, the nutraceutical composition contains a safe and effective amount (such as 0.01-99 wt %) of m-amidobenzamide derivatives or their nutraceutical acceptable salts, esters, extracts or acceptable carriers.

The nutraceutical product composition of the present invention may contain the same content of the m-amidobenzamide derivatives or their nutraceutical acceptable salts, esters, or extracts in the same content as the pharmaceutical composition.

Generally, the content of the mid-amidobenzamide derivative in the nutraceutical acceptable composition can be slightly lower, for example, containing 0.01-50 wt % of the mid-amidobenzamide derivative or its pharmaceutically acceptable salt or ester.

The nutraceutical acceptable composition of the present invention can be made into any conventional formulations by conventional methods, preferably tablet formulations, oral liquid formulations, granules and capsule formulations.

4. Food Additives

In addition to preparing pharmaceutical compositions for the treatment of tumors and as nutraceutical composition for adjuvant treatment of tumors, in the present invention, m-amidobenzamide derivatives or their nutraceutical acceptable salts or esters or extracts can be used to prepare food additives, and can be added to food, improve the anti-tumor ability of the subject and assist in the treatment of tumors.

In the present invention, the food additive may contain a safe and effective amount (such as 0.01-99 wt %) of the m-amidobenzamide derivative or a food acceptable salt or ester or extract thereof, and a food acceptable carrier.

The food additive of the present invention may contain the same content of the m-amidobenzamide derivative or its food acceptable salt, ester or extract as the pharmaceutical composition or the nutraceutical composition. Generally, the content of the m-amidobenzamide derivative as the food additive can be lower than that in the nutraceutical composition, for example, containing 0.01-50 wt % of the m-amidobenzamide derivative or a food acceptable salt or ester thereof.

In addition, it is also feasible to directly use the m-amidobenzamide derivatives of the present invention or their food-acceptable salts or esters or extracts as food additives under appropriate circumstances, as long as they do not affect the food quality, taste and/or appearance.

The food additive of the present invention can be made into any conventional form by conventional methods, such as solution, powder, syrup and the like.

In order to make the above objects, features and advantages of the present invention more obvious and easier to understand, the technical solutions of the present invention are further described below with reference to the embodiments. However, the present invention is not limited to the listed embodiments, but also includes any other known modifications within the scope of the claimed rights of the present invention.

Reference herein to "one embodiment" or "an embodiment" refers to a particular feature, structure, or characteristic that may be included in at least one implementation of the present invention. The appearances of "in one embodiment" in various places in this specification are not all referring to the same embodiment, nor are they separate or selectively mutually exclusive from other embodiments.

The experimental method of unreceipted specific conditions in the following examples, usually according to normal conditions, such as people such as Sambrook, "Molecular Cloning: Laboratory Manual" (New York, Cold Spring Harbor Laboratory Press, New York: Cold Spring Harbor Laboratory Press, 1989), or as suggested by the manufacturer.

Percentages and parts are by weight unless otherwise indicated. Unless otherwise defined, all professional and scientific terms used herein have the same meanings as those familiar to those skilled in the art. In addition, any methods and materials similar or equivalent to those described can be used in the present invention. Methods and materials for preferred embodiments described herein are provided for illustrative purposes only.

Cell Lines

SKOV3 cell line: purchased from ATCC, an ovarian cancer tumor cell line that positively expresses NAC1.

The culture method of SKOV3 cell line was as follows: the cells were inoculated in DMEM (InVitrogen) medium containing 10% calf serum, and placed in a $CO_2$ incubator with a volume fraction of 5% at 37° C., cultivated for two weeks.

EXAMPLES

1. Screening of Small Molecule Compounds (NAI-008)

A computer-assisted virtual screening method was used. First, the dimer structure of the POZ domain of NAC1 was obtained from the RCSB PDB, the binding mode of the dimer was analyzed, and the surface shape and hydrophilic and hydrophobic properties of the receptor were calculated using the SiteFinder function of MOE to determine the most suitable small molecule inhibitor. The combined active sites were pretreated for more than 10 designed compounds, and the ADMET properties of the compounds were filtered using Oprea's leadlikeness filter to retain molecules suitable as lead compounds. Energy minimization was performed for each compound separately, and then rigid and flexible docking methods were used in turn to dock small molecules to the aforementioned active sites of the receptors. To calculate the binding free energy, molecules with binding energies below −10 kcal/mol were selected, calculating the molecular topological fingerprints, performing cluster analysis according to the Tanimoto similarity between fingerprints, obtaining comprehensive score and structure diversity to extract structural diversity subsets, and selecting the final candidate based on the visual judgment of the receptor-ligand interaction mode molecular.

Among them, NAI-008 small molecule compound (4-((2-(4-(tert-butyl)phenoxy)-acetyl)glycyl)phenylbenzo[d][1,3] dioxane was selected. The structural formula is Formula I:

(Formula I)

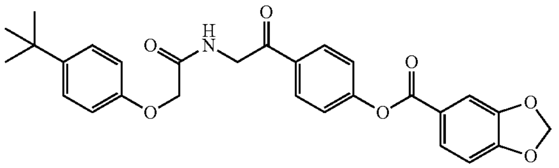

2. The Synthetic Route of the Small Molecule Compound (NAI-008) is as Follows:

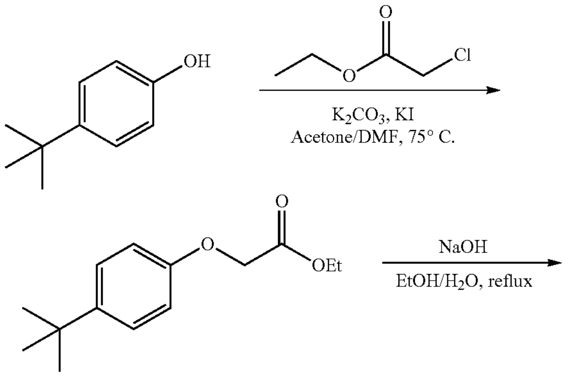

-continued

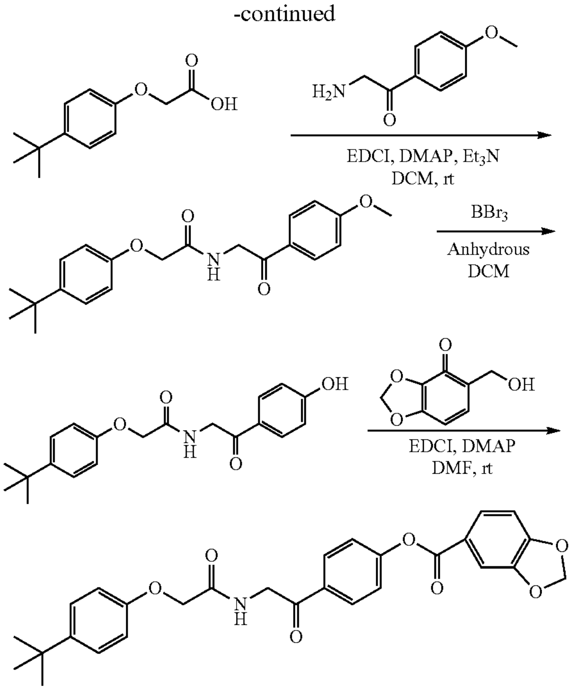

NAI-008

Using p-tert-butylphenol as starting material, it was condensed with ethoxyacetyl chloride under alkaline conditions, and hydrolyzed under alkaline conditions to free the carboxyl group. The carboxyl group was condensed with p-methoxyphenylacetamide under the catalysis of EDCI, and further under the action of $BBr_3$, methyl protection was removed, and the free phenolic hydroxyl and carboxylic acid formed an ester to obtain the target molecule.

3. Small Molecule Compound (NAI-008) Inhibits Dimerization of the Target NAC1 Protein For the selected NAI-008 (self-synthesized), the dimer formation of the target NAC1 protein by small molecule compounds was detected by immunoprecipitation technology and immunoblotting.

The results confirmed that NAI-008 inhibits the formation of NAC1 protein dimer, as shown in FIG. 1.

4. Inhibition of Tumor Cell Growth and Proliferation by Small Molecule Compound (NAI-008)

This embodiment used a conventional MTT method. The specific method included following:

SKOV3 cells were plated overnight in 96-well plates at a density of 3000 cells/well. The small molecule compound NAI-008 was then added to the wells at various concentrations (1.25, 2.5, 5, 10, 20, 50 μM) alone or in combination with cisplatin of a final concentration of 20 μM. After 48 hours, 10 μl of MTT (5 mg/ml) was added to each well, and the supernatant was discarded after incubation at 37° C. for 4 hours. After dissolving the purple crystal with 150 μl of dimethyl sulfoxide, the plates were placed in a microplate reader (Bio-Rad Company) to detect the absorbance at 570 nm.

In this example, conventional clonal colony formation experiments were used. The specific method included the following:

SKOV3 cells were treated according to the experimental requirements for 24-48 hours, digested with trypsin, and the cell suspension was repeatedly pipetted to make the cells fully dispersed. The percentage of single cells were above 95%, and counted on a hemocytometer. Based on a concentration of 2000 cells per dish, 2 ml of cell suspension was inoculated into the culture dish, so that the cells were evenly dispersed. Culturing in 37° C., 5% $CO_2$ for 7 to 14 days, with fresh medium from time to time. Observation under an inverted microscope. When macroscopic colonies appeared in the petri dish, the culture was terminated, the medium was discarded, and PBS was used to rinse twice. Crystal violet staining for 20 minutes. The results were analyzed after 2-3 washes with PBS.

Figure 2A:
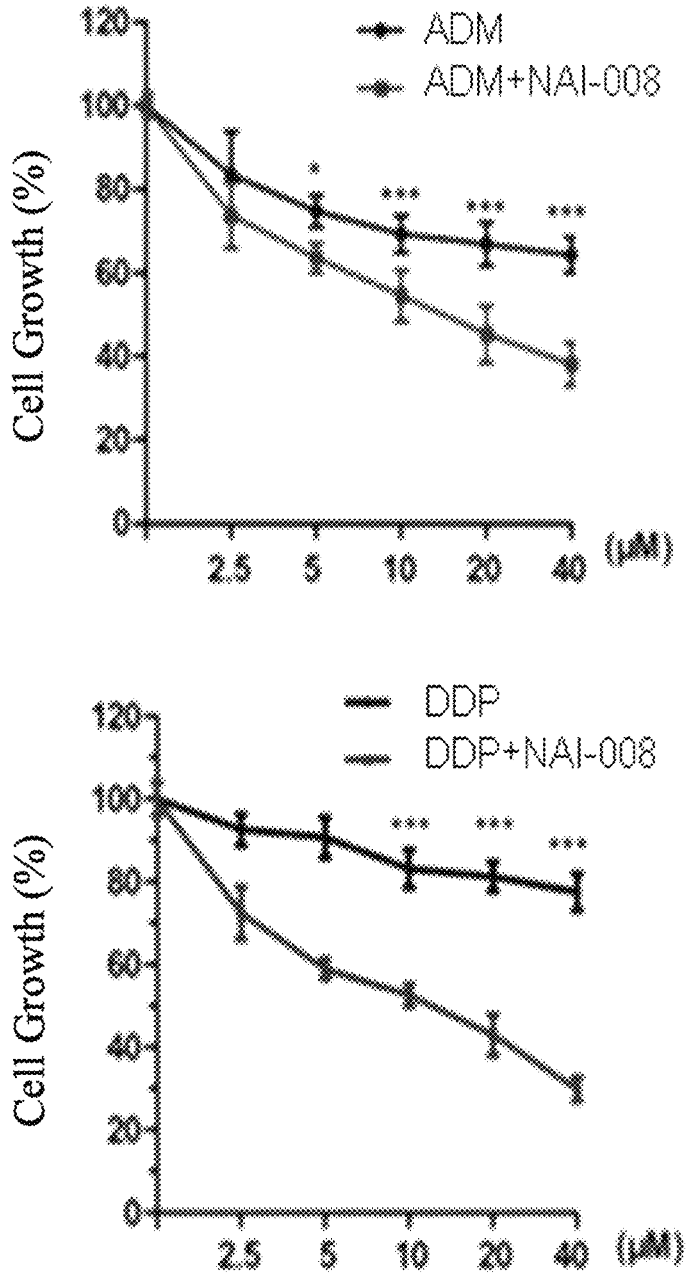
FIG. 2A shows that compound NAI-008 enhances the cell growth inhibition of cisplatin and doxorubicin, and the concentration of the compound used is 20 μM and the concentration of cisplatin and doxorubicin is 0-40 μM.
Figure 2B:
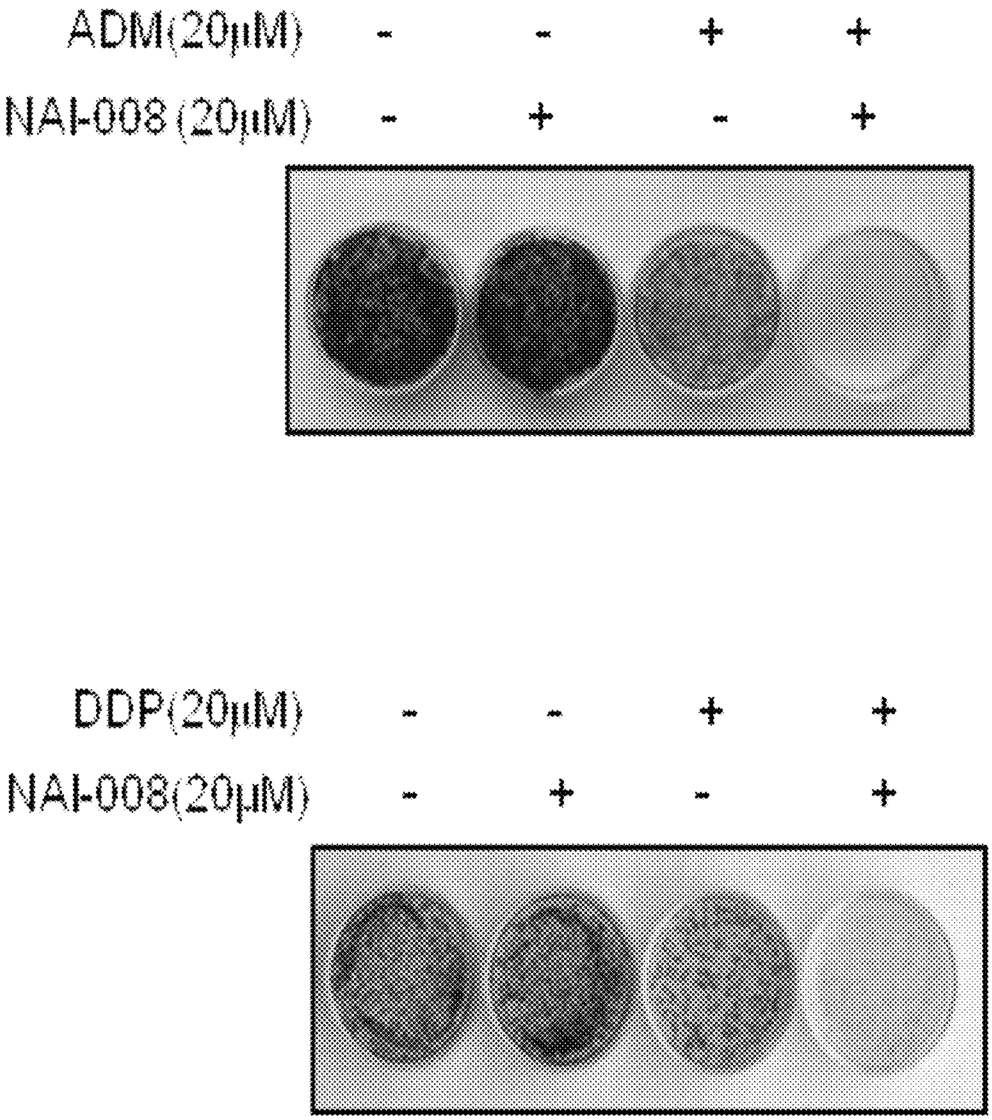
FIG. 2B shows that NAI-008 enhances the cell proliferation inhibition of cisplatin and doxorubicin, and the concentration of the compound used is 20 μM and the concentration of cisplatin and doxorubicin is 0-40 μM.

The results showed that NAI-008 significantly enhances the inhibition of cell growth and proliferation by cisplatin and doxorubicin at a final concentration of 20 uM, while its single application did not cause significant toxic effects on cells, as shown in FIGS. 2A and 2B.

Figure 2C:
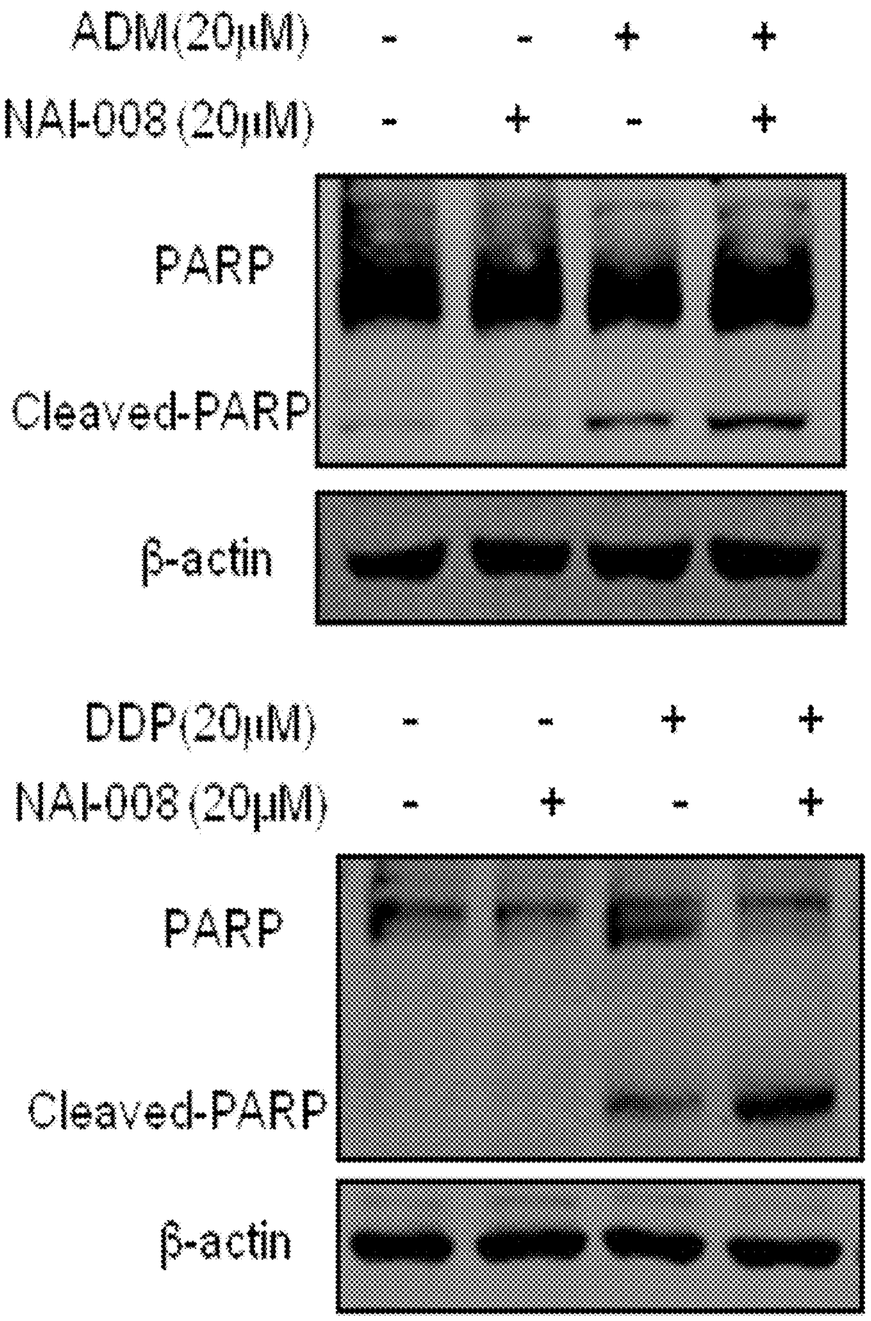
FIG. 2C shows that the compound NAI-008 enhances cisplatin- and doxorubicin-induced apoptosis, and the concentration of compound is 20 μM and the concentration of cisplatin of 20 μM.

5. Detection of Enhanced Effect of Small Molecule Compound (NAI-008) on Tumor Cell Killing by Cisplatin and Doxorubicin The ovarian cancer cell line SKOV3 cells were plated into 24-well plates at a density of 20,000 cells/well, and after 16-24 hours of incubation, NAI-008 was added to a final concentration of 20 μM. After 4 hours, additional cisplatin or doxorubicin was added to a final concentration of 20 μM. After 48 hours, the expression of PARP cleaved by apoptotic protein was detected by immunoblotting. The results are shown in FIG. 2C: the expression of apoptotic proteins was significantly higher in cells treated with cisplatin or doxorubicin 20 μM and NAI-008 20 μM than in cells treated with cisplatin or doxorubicin alone. Furthermore, consistent with the MTT results: the compound alone did not cause significant apoptosis.

The compound of the present invention specifically inhibits the formation of human nucleus accumbens 1 protein dimer, so it can be used to treat tumors with high expression of this protein, such as ovarian cancer.

The results of the above examples of the present invention show that the compound of the present invention can stably inhibit NAC1, and synergize with cisplatin or doxorubicin to kill tumor cells.

It should be noted that 2-(4-tert-butylphenoxy)-N-(2-{[(4-tert-butylphenoxy)-acetyl]amino}ethyl)acetamide and NAI-008 are two compounds with completely different core structures. The former includes acylated ethylenediamine as the main effect structure, and the latter includes acylated phenoxyacetamide as the main effect structure. The relationship between the two is not a simple derivative. They have completely different type of structures.

In summary, the present invention discloses an anti-tumor small molecule compound targeting human nucleus accumbens 1 and a composition thereof, which can effectively target and inhibit the anti-apoptotic molecule-NAC1 protein, and be used for cancer treatment. It can also be combined with other drugs and treatment methods for the treatment of malignant tumors; it has the advantages of good permeability, lower toxic and side effects, simple structure and synthetic route.

It should be noted that the above embodiments are only used to illustrate the technical solutions of the present invention and not to limit them. Although the present invention has been described in detail with reference to the preferred embodiments, those of ordinary skill in the art should understand that the technical solutions of the present invention can be modified, and equivalent substitutions without departing from the spirit and scope of the technical solutions of the present invention should be included in the scope of the claims of the present invention.

The invention claimed is:

1. 4-((2-(4-(tert-butyl)phenoxy)acetyl)glycyl)phenylbenzo[d][1,3]dioxane-5-carboxylate, having the following structure:

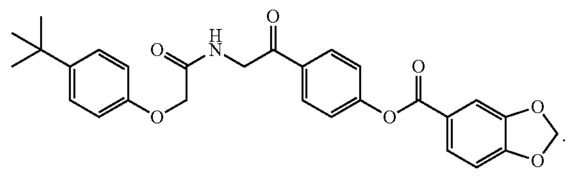 [SMILES: CC(C)(C)c1ccc(OCC(=O)NCC(=O)c2ccc(OC(=O)c3ccc4c(c3)OCO4)cc2)cc1]

2. A method of preparing 4-((2-(4-(tert-butyl)phenoxy)acetyl)glycyl)phenylbenzo[d][1,3]dioxane-5-carboxylate of claim 1 comprising the following synthetic route:

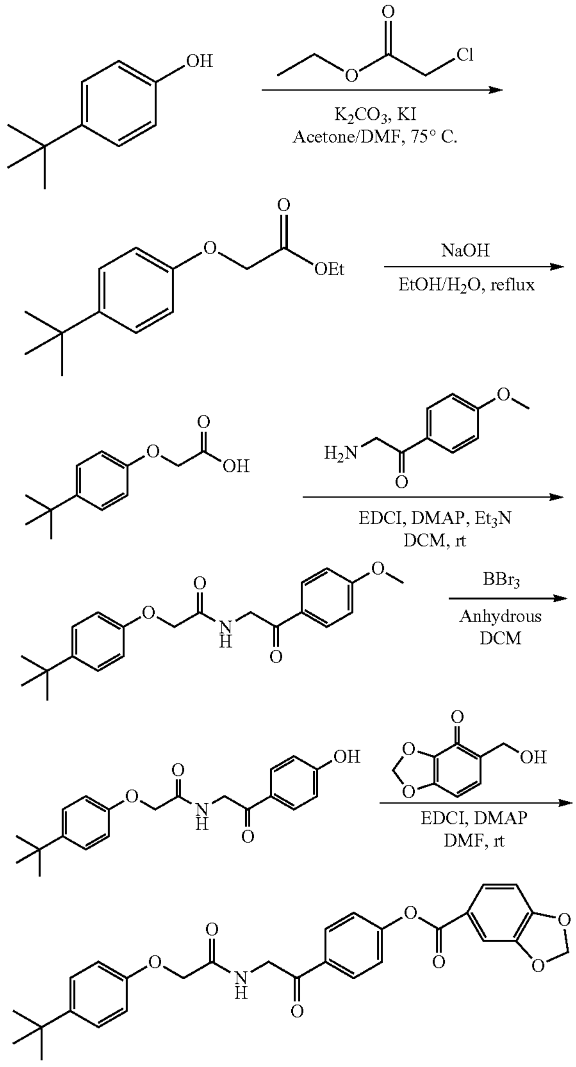

NAI-008

3. A method of treating a tumor, inhibiting tumor cell growth, and/or inducing tumor cell apoptosis in a patient in need thereof comprising administering a therapeutically effective amount of 4-((2-(4-(tert-butyl)phenoxy)acetyl)

glycyl)phenylbenzo[d][1,3]-dioxane-5-carboxylate, or a pharmaceutical, nutraceutical or food science acceptable salt thereof.

4. The method according to claim 3, wherein the tumor or tumor cell expresses human nucleus accumbens 1, and the expression level of the human nucleus accumbens 1 of the tumor or tumor cell is 30%-50% higher than that of a normal cell.

5. The method according to claim 3, wherein the tumor or tumor cell is selected from the group consisting of an ovarian cancer tumor or tumor cell, a cervical cancer tumor or tumor cell, a breast cancer tumor or tumor cell, and an endometrial cancer tumor or tumor cell.

6. A composition, comprising:

(1) 4-((2-(4-(tert-butyl)phenoxy)acetyl)glycyl)phenylbenzo[d][1,3]-dioxane-5-carboxylate, or a pharmaceutical, nutraceutical or food science acceptable salt thereof;

(2) an apoptotic drug; and (3) a pharmaceutical, nutraceutical, or food science acceptable carrier or excipient.

7. The composition according to claim 6, wherein the apoptotic drug is cisplatin or doxorubicin.

8. The composition according to claim 6, wherein the weight ratio of 4-((2-(4-(tert-butyl)phenoxy)acetyl)glycyl)phenylbenzo[d][1,3]-dioxane-5-carboxylate and the apoptotic drug is 1:50-50:1.

9. The composition according to claim 6, wherein 4-((2-(4-(tert-butyl)phenoxy)acetyl)glycyl)phenylbenzo[d][1,3]-dioxane-5-carboxylate is 10-80 wt % of the total weight of the composition.

10. The composition according to claim 6, wherein a dosage form of the composition is a tablet, capsule, powder, granule, suspension, or injection.

* * * * *